US00PP35134P2

(12) United States Plant Patent
Hansen

(10) Patent No.: US PP35,134 P2
(45) Date of Patent: Apr. 25, 2023

(54) ***HOSTA* PLANT NAMED 'LONE STAR'**

(50) Latin Name: ***Hosta* hybrid**
Varietal Denomination: Lone Star

(71) Applicant: Hans A Hansen, Zeeland, MI (US)

(72) Inventor: Hans A Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 0 days.

(21) Appl. No.: 17/803,733

(22) Filed: Nov. 1, 2022

(51) Int. Cl.
*A01H 5/02* (2018.01)
*A01H 6/12* (2018.01)

(52) U.S. Cl.
USPC ..... Plt./353
CPC ..... *A01H 6/12* (2018.05)

(58) Field of Classification Search
USPC ..... Plt./353
CPC ..... A01H 5/02
See application file for complete search history.

*Primary Examiner* — Kent L Bell

(57) ABSTRACT

A new and distinct *Hosta* plant named 'Lone Star' with large, broadly-mounded habit of heavy-substance, stiff, variegated foliage. Leaves are glaucous, ovate with coarsely, weakly undulate, yellowish-chartreuse margins, medium-green centers, and intermediate colors between. Flowers are pale lavender, held well out around foliage beginning in early July. The new plant is attractive for landscaping in the garden as a specimen, in mass and as a large container plant.

2 Drawing Sheets

Latin name and variety denomination of the plant:
Botanical classification: *Hosta* hybrid.
Variety denomination: 'Lone Star'.

STATEMENT REGARDING PRIOR DISCLOSURES UNDER 37 CFR 1.77(b)(6)

*Hosta* 'Lone Star' was first introduced by the inventor as a non-enabling description through the International Cultivar Registration Authority registration in early 2021. No plants of *Hosta* 'Lone Star' have been sold, in this country or anywhere in the world, nor has any enabling disclosure of the new plant been made, more than one year prior the filing date of this application.

BACKGROUND AND ORIGIN OF THE PLANT

The present invention relates to a new and distinct *Hosta* plant, *Hosta* 'Lone Star' hereinafter also referred to as the new plant or by the cultivar name, 'Lone Star'. *Hosta* 'Lone Star' is a whole plant mutation of 'Key West' (not patented) discovered by the inventor at a wholesale perennial nursery in Zeeland, Mich., USA on Jul. 10, 2017. The new plant was assigned the code 17-SP-HOST-617 and passed the initial evaluation in the summer of 2018. The new plant has been asexually propagated by division at the same nursery in Zeeland, Mich., USA since 2019 and also by careful plant shoot-tip tissue culture with the resultant asexually propagated plants having retained all the same traits as the original plant. *Hosta* 'Lone Star' has been stable and reproduces true to type plants in successive generations of asexual reproduction.

BRIEF SUMMARY OF THE PLANT

There are over 7,000 registered and established *Hosta* cultivars recognized by The American *Hosta* Society, which is the International Cultivar Registration Authority for the genus *Hosta*. The nearest comparison cultivars known to the inventor are: 'Abba Dabba Do' (not patented), 'Afternoon Delight' (not patented), 'American Icon' U.S. Plant Pat. No. 17,441, 'Atlantis' U.S. Plant Pat. No. 17,093, 'Climax' (not patented), and 'Drop-dead Gorgeous' U.S. Plant Pat. No. 33,318, 'Fortunei Aureomarginata' (not patented), 'Goodness Gracious' U.S. Plant Pat. No. 23,081, 'Ming Treasure' (not patented), 'Miss Tokyo' (not patented) 'One Last Dance' U.S. Plant Pat. No. 30,000, 'Spartacus' (not patented), and 'Terms of Endearment' U.S. Plant Pat. No. 34,806.

All of the above plants have a medium to large-size habit and foliage with a green center and a yellowish variegated margin. 'Abba Dabba Do' has narrower foliage with a narrower variegated yellow margin and the scapes are shorter and more erect. 'Afternoon Delight' has more cordate and bullate foliage, and the flowers are near white. 'Atlantis' has a larger habit, larger foliage that has a downward curl toward the more acute apex, with a more acute apex, and more undulation in the margin. 'Climax' has a more upright habit, and the leaves are more cordate and more bullate. 'Fortunei Aureomarginata' has medium-sized habit, foliage that is more cordate, leaf margins are narrower, and the flowers are more purple on more upright scapes. 'Goodness Gracious' has more cordate, more bullate, more sinuate foliage with a much wider margin, and the flowering season starts earlier. 'Ming Treasure' has a more lustrous leaf surface, with a narrower margin, the flowers are larger, fragrant, white, on a shorter scape. 'Miss Tokyo' has a rounder to more cordate leaf shape and the margin is narrower. 'One Last Dance' has a larger habit, the foliage is larger and more sinuate, 'Spartacus' has a larger habit, and larger, more sinuate, the apex is more acute with a slight twist, the center is darker green, and the scapes are taller and more erect with more persistent and larger foliar bracts. 'Terms of Endearment' has leaves that have a more cordate base, a more broadly acute apex, the margins that start the spring more chartreuse and mature to more creamy-yellow, and the center is more bluish-green.

The sport parent has leaves that are solid yellowish-colored with similar habit, size and flowering.

Other *Hosta* cultivars may have similar colored variegated foliage, but 'Lone Star' is distinct from the above-listed *Hostas* and all other cultivars known to the inventor by the following combined traits:

1. Large-sized, broadly-mounded plant habit with heavy-substance, flat, stiff foliage;
2. Matte leaves are ovate with weakly and coarsely undulate margin;
3. Leaf centers are medium green and the variegated margins are yellowish-chartreuse with intermediate colors between;
4. Medium-sized flowers are on tall scapes arching well over and around foliage;
5. Tepals are pale lavender with slightly darker veins and translucent margins.

BRIEF DESCRIPTION OF THE DRAWINGS

The photographs of the new plant demonstrate the overall appearance of the new plant, including the unique traits. The colors are as accurate as reasonably possible with color reproductions. Ambient light spectrum, temperature, source and direction may cause the appearance of minor variation in color. The drawings show a five-year-old 'Lone Star' plant in a trial garden at a nursery in Zeeland, Mich. with supplement fertilizer and water as needed.

DETAILED BOTANICAL DESCRIPTION

Figure 1:
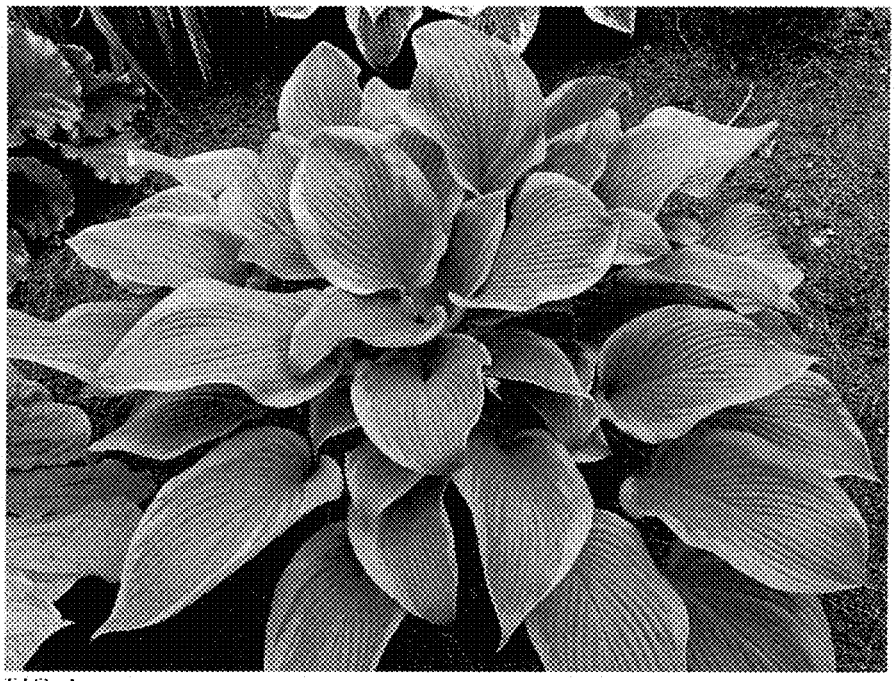
FIG. 1 shows the habit of a five-year-old plant.
Figure 2:
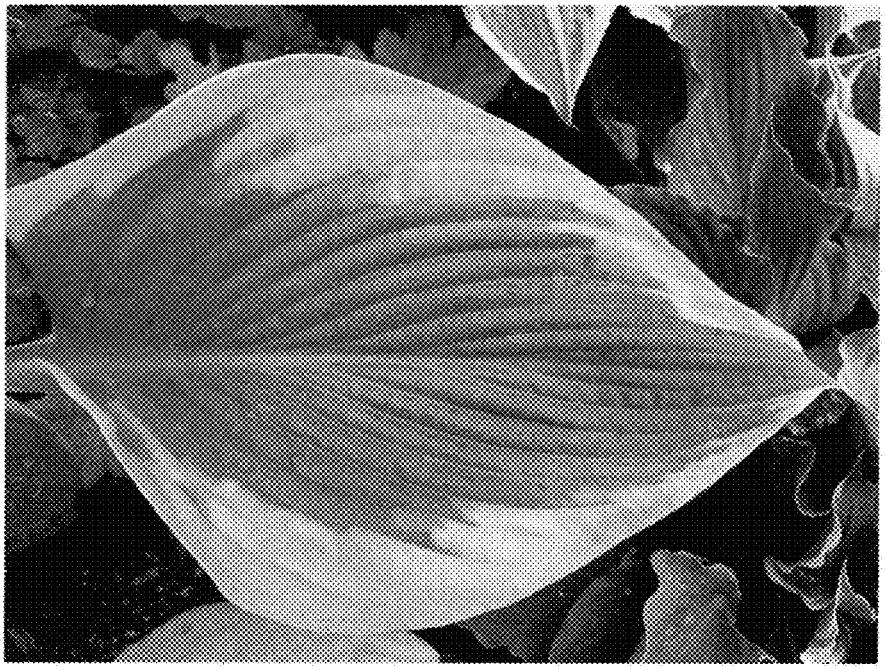
FIG. 2 shows a close-up of the foliage with variegation.
Figure 3:
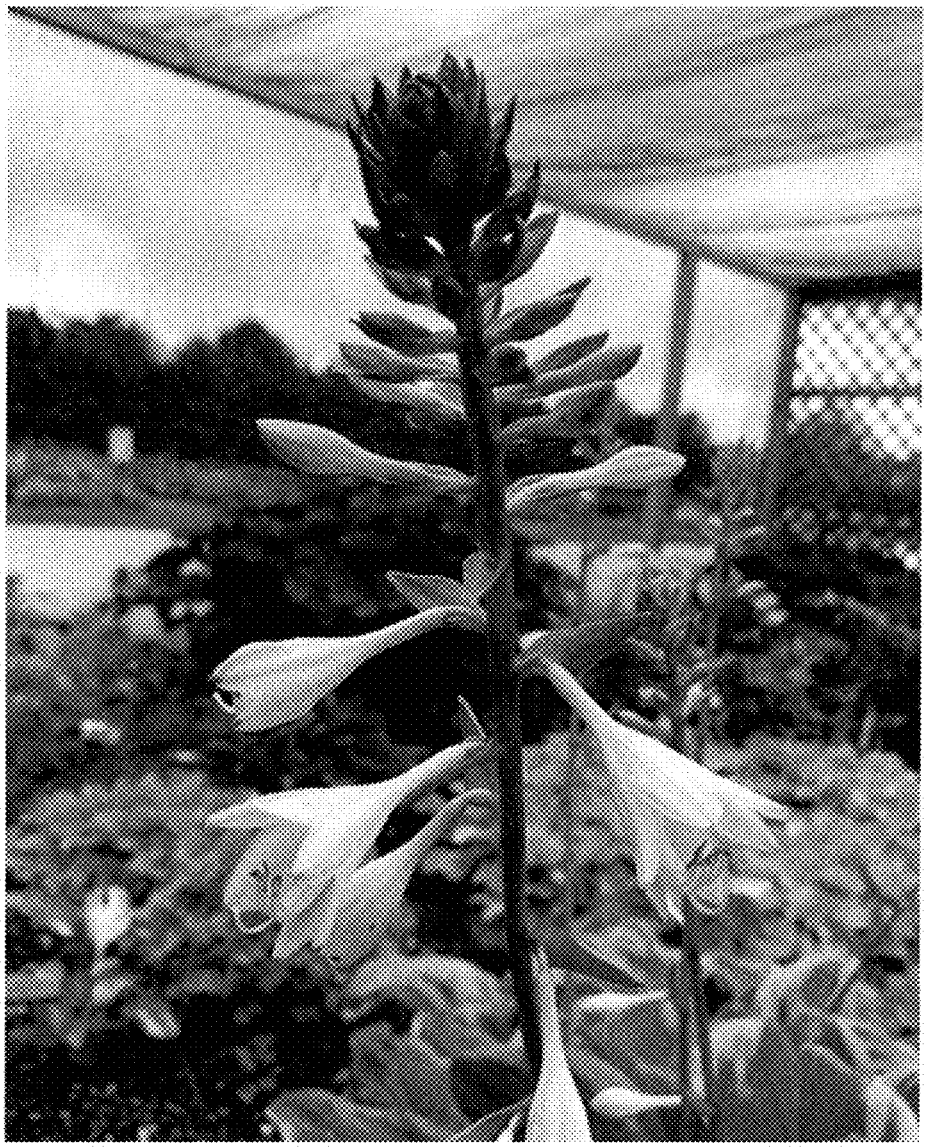
FIG. 3 shows a close-up of the flowers.

The following descriptions and color references are based on the 2015 edition of The Royal Horticultural Society Colour Chart except where common dictionary terms are used. The new plant, *Hosta* 'Lone Star', has not been observed in all possible environments. The phenotype may vary slightly with different environmental conditions, such as temperature, light, fertility, moisture, and maturity levels, but without any change in the genotype. The following observations and size descriptions are of a five-year-old plant in a partially shaded trial garden in Zeeland, Mich. with supplemental water and fertilizer.

Botanical classification: *Hosta* hybrid;

Parentage: A whole uninduced sport of 'Key West';

Propagation: Garden division and sterile shoot-tip tissue culture;

Time to initiate roots from tissue culture: About two to three weeks;

Growth rate: Rapid;

Crop time: About 10 to 12 weeks to finish during the summer in a one-liter container from rooted tissue culture plantlet;

Rooting habit: Normal, fleshy, lightly branching; color between RHS NN155A and RHS NN155B depending on soil content;

Plant shape and habit: Hardy herbaceous perennial with basal rosettes of leaves emerging from rhizomes producing a large, symmetrical, broad mound of leaves; about 10 divisions per plant with 6 flowering scapes; divisions to about 3 cm diameter at soil level;

Plant size: Foliage height about 66 cm above soil line to the top of the leaves and about 132 cm wide at the widest point about 30 cm above the soil line;

Foliage description: Ovate; acute apex; cordate to rounded base; entire margin; glabrous and matte adaxial, and glabrous and lustrous becoming matte abaxial; blades mostly flat with coarse, weakly undulate margin;

Leaf blade size: To about 29 cm long, 20 cm wide at base; average about 26 cm long and 18 cm wide; with variegated yellowish-chartreuse margin of variable width between 1.3 cm and 3 cm wide;

Leaf blade color: Early season and expanding adaxial margin between RHS 145A and RHS 146D, adaxial center nearest RHS 138B, with intermediate colors between the margin and center comprising between RHS 147C and RHS 146D, and between RHS 148C and RHS 145B; early season and expanding abaxial margin between RHS 145A and RHS 145B, and center nearest RHS 146B with intermediate colors comprising RHS 146D, and between RHS 193B and RHS 147D without noticeable abaxial intermediate colors; mid-season and later summer adaxial margin between RHS N144A and RHS 146D, center nearest RHS 137B, intermediate region variable comprising RHS 144A, and RHS 143C; mid-season and later summer abaxial margin nearest RHS 146D, center between RHS 138A and RHS 137B, between margin and center intermediate colors comprising between RHS 146D and RHS 145A, and between RHS N144A and RHS 145A;

Petiole: Glabrous, deeply concavo-convex; stiff, strong and slightly flexible; mostly straight from base of plant to leaf base with little bending or arching; to about 52 cm long and 18 mm wide and 12 mm deep at base;

Petiole color: Adaxial and abaxial margin about 1 mm wide nearest RHS 146D, abaxial center nearest RHS 145D with marginal 2 mm between RHS 138B and RHS 138A;

Veins: Parallel, moderately impressed adaxial, moderately bulging between veins; strongly costate and smooth abaxial side; about 13 to 15 pairs and one midrib;

Veins color: Adaxial margin nearest RHS 138B, center nearest RHS 138A; abaxial midrib nearest RHS 145D, primary veins in center region nearest RHS 148D, and marginal veins nearest 146D;

Flower description: Perfect; single; actinomorphic; funnel-form to campanulate; held outwardly to slightly drooping; mostly secund; persist for normal period, usually one day on plant or as cut flower; about 55 flowers per scape;

Flower period: Scapes remain effective with flowering beginning early July for about four to five weeks in Michigan;

Flower size: To about 55 mm long to exserted style; corolla to about 48 mm long and to about 22 mm across at apex; distal bell portion 28 mm long and gradually tapering to corolla tube; corolla tube to about 20 mm long and 4 mm diameter toward base;

Fragrance: None detected;

Floral bracts: Subtending individual flowers; lanceolate; acute apex, truncate clasping base, margin entire; glabrous adaxial and abaxial; projecting about 90° from scape in proximal scape and about 45° from scape in distal portion; to about 44 mm long and 17 mm across near base, decreasing in size distally; drying two to three days after flower dehisces;

Bract color: Proximal bracts adaxial center one-third nearest RHS 145D and margin portion nearest RHS 145B, abaxial between RHS 145A and RHS 146D, distal adaxial color variable, nearest RHS 146C with random portions nearest RHS N187B, distal abaxial color variable, nearest RHS 146C with random portions nearest RHS N187B;

Tepals: Two sets of three; lanceolate with acute apex and fused base;

*Inner set.*—48 mm long and 11 mm across slightly above fusion; fused in basal 33 mm and free in distal 15 mm; translucent and vitreous along 1 mm wide margin.

*Inner set color.*—Adaxial center three veins in distal bulb portion nearest RHS 84D, 1 mm translucent to clear margin, center 3 mm between RHS 84D and RHS NN155D, bulb portion between clear margin and center nearest RHS NN155D; abaxial bulb portion lighter than a blend between RHS 84D and RHS NN155D and tube portion nearest RHS 84D.

*Outer tepal.*—48 mm long and 9 mm across slightly above fusion; fused in basal 33 mm and free in distal 15 mm.

*Outer tepal color.*—Adaxial 4 mm wide center between RHS 84D and RHS NN155D, abaxial distal bulb portion closer to RHS NN155D than to RHS 84D, corolla tube nearest RHS 84D.

Gynoecium: Single; tri-carpelled; 57 mm long;

*Style.*—Single; cylindrical; arcuate upward to recurved greater than 90° in distal 9 mm; about 46 mm long and 1 mm diameter; color RHS NN155B.

*Stigma.*—Flattened tri-lobed, micro-puberulent; about 1.5 mm across and 1 mm long; color nearest RHS NN155B.

*Ovary.*—Superior; oblong ellipsoidal; rounded apex and truncate base; shallowly longitudinally fluted; about 10 mm long and 3.5 mm diameter; color between RHS 146D and RHS 145A.

Androecium: Six;

*Filaments.*—Six; cylindrical; glabrous; recurved about 120° in distal 8 mm portion; about 50 mm long and 1 mm diameter; color nearest RHS NN155B.

*Anthers.*—Oblong; dorsifixed, longitudinally dehiscent; about 4 mm long, 2.5 mm across, and 1.5 mm thick; color adaxial between RHS 163B and RHS 164B and abaxial between RHS 158A and RHS 160D.

*Pollen.*—Smaller than 0.1 mm diameter; color nearest RHS 17A.

Flower bud: Clavate; with acute apex and fused tubular base; about 39 mm long in total and 9 mm wide in bulb portion, tube about 14 mm long and 3 mm diameter;

Flower bud color: Nearest RHS 84D in bulb and tube between RHS 84D and RHS NN155C;

Pedicel: Cylindrical, glabrous, slightly glaucous; outwardly to slightly drooping; mostly secund; to about 10 mm long and 2 mm diameter;

Pedicel color: Between RHS 192D and RHS 148D;

Peduncle: Cylindrical; usually one per mature division and five per plant; strongly glaucous; glabrous; stiff, rigid; arching; to about 142 cm long and about 9 mm diameter at base; flowering in upper 52 cm with about 55 flowers per scape; flower spacing proximally to 8.5 cm and distally as close as 2 mm;

Peduncle color: Between RHS 146B and RHS 146C with a faint blush of nearest RHS 84A distally;

Fruit: Non-fleshy, dehiscent, tri-loculicidal capsule; oblong to cylindrical with rounded apiculate apex and attenuate base; to about 35 mm long and 7 mm diameter;

Fruit color: Nearest RHS 146A as developing and nearest RHS 161D as mature;

Seed: Typically about 30 to 36 per capsule under natural conditions; endospermic; flattened-ellipsoidal wing surrounding embryo at one end of the wing; to about 11 mm long, 2 mm wide, and 1.5 mm thick at embryo;

Seed color: Nearest RHS 202A;

Disease and pest tolerance and resistance: The new plant has not shown any resistance to pests, including *Odocoileus virginianus* and *Oryctotagus cuniculus*, and diseases common to *Hostas*. Growth: The plant grows best and shows best coloration with plenty of moisture, adequate drainage and light shade, but is able to tolerate some drought when mature. Hardiness: at least from USDA zone 3 through 9. It is claimed:

1. A new and distinct ornamental *Hosta* plant named 'Lone Star' as herein described and illustrated.

* * * * *